(12) United States Patent
Fallon (10) Patent No.: US 9,587,471 B2
(45) Date of Patent: Mar. 7, 2017

(54) CONTROLLING BIOAVAILABILITY OF NUTRIENT ADDITIONS IN SUBSURFACE FORMATIONS

(71) Applicant: E I DU PONT DE NEMOURS AND COMPANY, Wilmington, DE (US)

(72) Inventor: Robert D Fallon, Elkton, MD (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 106 days.

(21) Appl. No.: 14/463,737

(22) Filed: Aug. 20, 2014

(65) Prior Publication Data

US 2014/0352946 A1   Dec. 4, 2014

Related U.S. Application Data

(62) Division of application No. 12/566,704, filed on Sep. 25, 2009, now Pat. No. 8,889,601.

(60) Provisional application No. 61/100,898, filed on Sep. 29, 2008.

(51) Int. Cl.

| C09K 8/582 | (2006.01) |
|---|---|
| C09K 8/68 | (2006.01) |
| E21B 43/16 | (2006.01) |
| A01N 31/02 | (2006.01) |
| A01N 31/08 | (2006.01) |
| A01N 33/04 | (2006.01) |
| A01N 33/12 | (2006.01) |
| A01N 35/02 | (2006.01) |
| A01N 37/02 | (2006.01) |
| A01N 37/40 | (2006.01) |
| A01N 47/14 | (2006.01) |
| A01N 47/28 | (2006.01) |
| A01N 59/00 | (2006.01) |

(52) U.S. Cl.
CPC .............. *E21B 43/16* (2013.01); *A01N 31/02* (2013.01); *A01N 31/08* (2013.01); *A01N 33/04* (2013.01); *A01N 33/12* (2013.01); *A01N 35/02* (2013.01); *A01N 37/02* (2013.01); *A01N 37/40* (2013.01); *A01N 47/14* (2013.01); *A01N 47/28* (2013.01); *A01N 59/00* (2013.01); *C09K 8/582* (2013.01)

(58) Field of Classification Search
None
See application file for complete search history.

(56) References Cited

U.S. PATENT DOCUMENTS

| 4,049,559 A | * | 9/1977 | Grier .................... A01N 33/04 166/400 |
|---|---|---|---|
| 4,286,660 A | | 9/1981 | Wagner et al. |
| 4,947,932 A | | 8/1990 | Silver et al. |

(Continued)

FOREIGN PATENT DOCUMENTS

RU   2170815 C1   7/2001

OTHER PUBLICATIONS

International Search Report dated Nov. 26, 2009, International Application No. PCT/US2009/058532.

(Continued)

*Primary Examiner* — John J Figueroa (57) ABSTRACT

Controlling microbial growth and activity during Microbial Enhanced Oil Recovery processes is disclosed. Specific control of microbial growth and activity in this process results in prevention of nutrient loss in transit and allows better targeting of microbial activity to the desired subsurface location(s).

4 Claims, 6 Drawing Sheets

(56) References Cited

U.S. PATENT DOCUMENTS

| | | |
|---|---|---|
| 7,472,747 B1 | 1/2009 | Brigmon et al. |
| 2007/0092930 A1 | 4/2007 | Lal et al. |
| 2007/0251146 A1 | 11/2007 | Larter et al. |
| 2008/0283242 A1 | 11/2008 | Ekstrand et al. |
| 2010/0044031 A1 | 2/2010 | Fallon et al. |

OTHER PUBLICATIONS

Kianipey, S. A. et al., Mechanisms of Oil Displacement by Microorganisms, SPE 15601, 1986, pp. 1-13, Society of Petroleum Engineers.
Brown, L. R. et al., Slowing Production Decline and Extending the Economic Life of an Oil Field: New MEOR Technology, SPE 59306, 2000, pp. 1-16, Society of Petroleum Engineers.
Sunde, Egil et al., Aerobic Microbial Enhanced Oil Recovery for Offshore Use, SPE/DOE 24204, 1992, pp. 497-502, Society of Petroleum Engineers/U.S. Department of Energy.
Silliker, J. H. et al., Microbial Ecology of Foods, Factors Affecting Life and Death of Microorganisms, 1980, pp. 70-91, vol. 1, Academic Press.
Paulus, Wilfried, Directory of Microbiocides for the Protection of Materials, A Handbook, 2005, pp. 157-176 and 444-773, Sringer-Verlag.
Robinson, R. K. et al., (ed.), Encyclopedia of Food Microbiology, 1999, pp. 1710-1781, Academic Press, London.
Block, Seymour S. (ed.), Disinfection, Sterilization, & Preservation, 5th Edition, 2001, Chapters 12, 13, and 14, pp. 229-320, Lippincott Williams & Wilkins.

\* cited by examiner

CONTROLLING BIOAVAILABILITY OF NUTRIENT ADDITIONS IN SUBSURFACE FORMATIONS

This application is a division application claiming priority to the U.S. application Ser. No. 12/566,704 filed on Sep. 25, 2009, which in turn claims priority to the Provisional Patent Application 61/100,898, filed Sep. 29, 2008.

FIELD OF THE INVENTION

The field of the invention is in the art of controlling microbial growth and activity. Specifically this invention relates to improving the microbial activities or the products of microbial activities to improve oil recovery in waterflooded oil formations during Microbial Enhanced Oil Recovery processes. More specifically this invention relates to techniques that inhibit nutrient loss in transit, allowing better targeting of microbial activity to the desired subsurface location(s).

BACKGROUND OF THE INVENTION

The challenge to meet the ever-increasing demand for oil includes increasing crude oil recovery from heavy oil reservoirs. This challenge has resulted in expanding efforts to develop alternative cost efficient oil recovery processes (Kianipey, S. A. and Donaldson, E. C. 61$^{st}$ Annual Technical Conference and Exhibition, New Orleans, La., USA, Oct. 5-8, 1986). Heavy hydrocarbons in the form of petroleum deposits and oil reservoirs are distributed worldwide. These oil reserves are measured in the hundreds of billions of recoverable barrels. Because heavy crude oil has a relatively high viscosity, it is essentially immobile and cannot be easily recovered by conventional primary and secondary means.

Microbial Enhanced Oil Recovery (MEOR) is a methodology for increasing oil recovery by the action of microorganisms (Brown, L. R., Vadie, A. A., Stephen, O. J. SPE 59306, SPE/DOE Improved Oil Recovery Symposium, Oklahoma, 3-5 Apr. 2000). MEOR research and development is an ongoing effort directed to developing techniques to use microorganisms to modify crude oil properties to benefit oil recovery (Sunde. E., Beeder, J., Nilsen, R. K. Torsvik, T., SPE 24204, SPE/DOE 8$^{th}$ Symposium on enhanced Oil Recovery, Tulsa, Okla., USA, Apr. 22-24, 1992). In addition to MEOR activity, microbial treatment of underground formations can also be used to accelerate bioremediation processes for environmental clean up.

Microbial growth induced in the oil reservoir can lead to a number of changes in the reservoir chemistry resulting in improved oil recovery. These changes may include gas formation, acid formation, selective pore plugging, and alterations in partitioning of oil between petrologic and aqueous phases. MEOR processes are usually applied later in the life of oil recovery systems. When easily mobilized oil becomes depleted in the oil reservoir, water (injection water) is often injected into oil reservoirs to improve oil recovery. Injection water is also commonly used to introduce necessary components of a MEOR process into the reservoir. Because access to the reservoir is limited by the frequency and number of wells penetrating the underground formation, subterranean process control is often difficult. There is need therefore to control timing, location, and character of microbial activation in subterranean processes.

Controlled microbial growth allows better optimization of subterranean processes that are enhanced by microbial activity. For example, MEOR processes depend on microbial activity or the products of microbial activity to improve oil recovery in waterflooded oil formations. Furthermore, bioremediation of contaminated subsurface formations can be accelerated by inducing microbial activity. In situations illustrated by the examples below it is often desirable to target microbial activation to specific subsurface locations. This is often difficult because nutrients typically used to activate microbial activity in a targeted location may be consumed in transit by native microbial populations. Loss of nutrients in transit makes the overall process less efficient and more costly. In addition uncontrolled microbial growth can damage the subsurface formation, slowing subsurface water flow and increasing backpressure on the injection wells. In this disclosure, techniques to control activation of microbial growth upon injection into the subsurface formation to overcome the deficiencies described above are disclosed.

SUMMARY OF THE INVENTION

This invention offers a solution to the need for controlling microbial activation in MEOR and bioremediation processes and relies on formulations that are inhibitory, at applied concentrations, to both native and introduced microbes when applied to the application site. These formulations prevent microbial growth and activation until the inhibitory agent has dissipated.

The invention includes a formulation for improving MEOR recovery from a subsurface oil formation comprising a combination of a microbial growth inhibitor composition and nutrients wherein the microbial growth inhibitors provide for the bioavailability of said nutrients for microbial populations within the subsurface formation.

Accordingly the invention provides an injection site formulation comprising an inhibited nutrient composition at an oil well site. The inhibited nutrient composition may include an inhibitory concentration of at least one nutrient or a chemical inhibitor. Inhibitory activity is biocidal or biostatic.

In another embodiment the invention provides a method for activating subsurface microbes at a targeted location for improved oil recovery at an oil well site comprising:
  a. providing the injection site formulation of the invention
  b. injecting the injection site formulation of (a) at an injection site in the subsurface formation of the oil well site under conditions whereby the microbial growth is enhanced at a target site distant from the injection site.

In an alternate embodiment the invention provides a method of enhancing the growth of microbes at a targeted subsurface location comprising:
  a. providing a subsurface location comprising an injection site;
  b. providing the components of an inhibited nutrient composition selected from the group consisting of:
    i) nutrients;
    ii) chemical inhibitors; and
    iii) live microbial cultures;
  c. performing an analysis of site treatment parameters selected from the group consisting of; determining the dispersion rate of subsurface water from the injection site; analyzing the composition oil at the oil well site to determine absorption rates of the chemical inhibitors; and analyzing the composition of subterranean fluids for hydrolysis rates of the chemical inhibitors;
  d. formulating an inhibited nutrient composition on the basis of the analysis of step c) in such that injection of the inhibited nutrient composition in fluid at the injection site results in enhanced microbial growth at a target site distant from the injection site.

BRIEF DESCRIPTION OF THE FIGURES OF THE INVENTIONS

As illustrated in FIGS. 3 & 4, relative rates of nitrate+nitrite loss and cell growth (increase in colony forming units) is slower in the ethyl formate inhibited treatment until substantial ethyl formate hydrolysis has occurred.

BIOLOGICAL DEPOSITS

The following biological materials have been deposited with the American Type Culture Collection (ATCC), 10801 University Boulevard, Manassas, Va. 20110-2209, and bear the following designations, accession numbers and dates of deposit.

| Biological Material | Accession Number | Date of Deposit |
|---|---|---|
| *Pseudomonas stutzeri* strain LH4:15 | ATCC PTA-8823 | Dec. 4, 2007 |

DETAILED DESCRIPTION OF THE INVENTION

The present invention relates to the method for controlling microbial growth and activity to improve oil recovery in oil formations during MEOR processes. More specifically this invention relates to techniques that inhibit nutrient loss in transit, providing for increased bioavailability of nutrients, and allowing better targeting of microbial activity to the desired subsurface location(s). As such, the present invention may also be used for enhancing bioremediation of subsurface contaminated sites.

The following terms have been used in this disclosure to describe the invention:

The term "radial transport" means the tendency of fluid flowing from a point source into an unconfined porous medium to spread vertically and horizontally.

The term "advection with water flow" means movement due to flow, generally driven by pressure gradients.

The term "hydrodynamic dispersion" means mixing that results from turbulence driven by local, fine scale, pressure gradients.

The term "molecular diffusion" or "molecular diffusivity" means the movement of molecules from a region of higher concentration to one of lower concentration by random molecular motion.

The term "longitudinal dispersivity" means hydrodynamic dispersion aligned to the direction of bulk water flow.

The term "transverse dispersivity" means hydrodynamic dispersion perpendicular to the direction of bulk water flow.

The term "injection water" means that water is injected into the reservoir usually to increase pressure and thereby stimulate production at the oil well. This method is used to increase oil recovery from an existing reservoir.

The term "subsurface microbial population" and "subterranean microbial population" refer to any collection of viable microbes resident beneath the earth's surface.

The term "inhibited nutrient composition" (INC) means a composition comprising various nutrients and optionally chemical inhibitors of microbial growth. Microbial growth inhibition by the INC may either be due to the presence of specific chemical inhibitors or to the inhibitory concentration of one of more of the nutrients in the INC. The INC is effective at preventing growth of subterranean or subsurface microbial populations in the well bore and at the face of the oil formation. Methods of application of the INC typically allow for the dissipation of the inhibitory agents at depth in the oil formation and subsequent growth stimulation of the subterranean microbial populations away from the face of the oil reservoir formation.

The term "nutrients" is used in its broadest sense and includes inorganic or organic compounds required by a microorganism for growth or which facilitate growth. Nutrients useful in the present invention include, but are not limited to; growth substrates (compounds that supply mass and energy for cell growth); electron acceptors; nitrogen and phosphorus sources as well as various "trace nutrients" such as vitamins and metals. The term "nutrient delivery" refers to the method of applying the required nutrients to the desired subterranean microbial population, which includes, but is not limited to, adding the inhibited nutrient composition to the injection water stream.

The term "targeted nutrient delivery" refers to the use of inhibitory nutrient compositions to protect nutrients from consumption during storage and transit in order to allow efficient delivery to the desired subterranean target microbial population, i.e., subterranean microbial populations distant from the formation face.

The term "promote growth", refers to increases in cell mass, which is done in the instant invention through nutrient additions.

The term "microbial growth inhibitor" as used herein includes agents which act to preserve materials subject to alteration by microbial growth by killing, suppressing, or preventing growth of microorganisms. Microbial growth inhibitors are typically part of the INC. Microbial growth inhibitors may be chemical inhibitors such as industrial preservatives with known biostatic or biocial activity or may in the alternative be nutrients as described herein where the concentration of the nutrient is inhibitory to microbial growth.

The term "preservative" refers to any natural or synthetic chemical that is added to formulations to prevent microbial growth.

The term "waterflooding" or "water flooding" refers to injection of water commonly used to improve oil recovery from an oil well formation.

The term "injection site formulation" refers to a formulation comprising and inhibited nutrient composition containing various nutrients and/or chemical inhibitors (e.g. preservatives and the like) that are added to the fluid used at the injection site during oil recovery processes. Water is a common medium for the injection site formulation and is used in waterflooding applications. However other fluids may additionally be used in the injection site formulation including but not limited to gases, aqueous mixtures, solvents and polymers.

The term "bioavailability" refers to the extent of availability of a nutrient to metabolism by the microbial subsurface population.

The terms "subsurface oil formation" or "subterranean oil formation" or "oil formation" or "oil well formation" refer to any oil formation below the soil surface.

The terms "biostat" or "biostatic" refer to compounds that cause inhibition of growth of a microbial cell.

The terms "biocide or "biocidal" refer to compounds that kill a microbial cell.

The term "subsurface contaminated site" refers to any subsurface geological formation or any water-containing formations that has been contaminated with undesirable substances.

The term "target site" or "targeted subsurface location" refers to a subterranean site of an oil well or other site where an injection site formulation comprising an INC will act to enhance microbial growth. Target sites are typically some distance from the injection site where the injection site formulation is initially applied. Methods of formulating the INC so that microbial enhancement is effective at the target site and not at the initial injection site are described herein.

The term "site treatment parameters" will refer to those parameters and conditions of an oil well site that will impact the application of an INC to the site. Typical site treatment parameters will include, but are not limited to; the dispersion rate of subsurface water from the injection site; the composition oil at the oil well site to opposite absorption rates of chemical inhibitors that may be in the INC; and the composition of subterranean fluids (water, oil and water/oil mix) for hydrolysis rates of the chemical inhibitors.

The terms "trace nutrients" or "trace elements" or "trace metals" refer to compounds such as vitamin and metals that are usually required, in addition to growth substrate and nitrogen sources, for microbial growth and activity.

The terms "application site" or "injection site" refer to locations where the inhibited nutrient composition is either injected into or applied by an applicable means to the oil well or the subsurface contaminated site.

Control Of Microbial Growth And Activity

The present invention describes the application of microbial growth inhibitors within the context of an INC to preserve injected nutrients. These methods allow the stimulation of subterranean microbial populations deeper in the oil formation to improve MEOR and/or bioremediation process efficiency. The INC comprises nutrients, and/or inhibitors.

Nutrients

Nutrients, comprising growth stimulating components may include the following substances, alone or in combination (1) growth substrates added at greater than 0.01% w/v (3) an electron acceptor for microbial growth, added at greater than 0.01% w/v (4) a source of nitrogen for microbial growth, added at greater than 0.001% w/v (5) a source of phosphorous for microbial growth, added at greater than 0.001% w/v (6) a source of trace nutrients, such as vitamins & metals, added at greater than 0.0001% w/v.

Useful nutrients contemplated herein include those containing at least one of the following elements: C, H, O, P, N, S, Mg, Fe, or Ca. By way of example only, such inorganic compounds include $PO_4^{2-}$, $NH_4^+$, $NO_2^-$, $NO_3^-$, and $SO_4^{2-}$ amongst others. Growth substrates may include sugars, organic acids, alcohols, proteins, polysaccharides, fats, hydrocarbons or other organic materials known in the art of microbiology to be subject to microbial decomposition. Major nutrients containing nitrogen and phosphorus (non-limiting examples may include $NaNO_3$, $KNO_3$, $NH_4NO_3$, $Na_2HPO_4$, $K_2HPO_4$, $NH_4Cl$); vitamins (non-limiting examples may include folic acid, ascorbic acid, and riboflavin); trace elements (non-limiting examples may include B, Zn, Cu, Co, Mg, Mn, Fe, Mo, W, Ni, and Se); buffers for environmental controls; catalysts, including enzymes; and both natural and artificial electron acceptors (non-limiting examples may include $SO_4^{2-}$, $NO_3^{-2}$, $Fe^{+3}$, humic acid, mineral oxides, quinone compounds, $CO_2$, $O_2$, and combinations thereof).

In another embodiment of the invention one or more of the above listed nutrient compositions, is included at a high concentration such that it is inhibitory to microbial growth. Typically "high concentration" will mean the use of any of these nutrients in excess of 10% w/v. For example many salts, sugars, esters, and alcohols are consumed for growth at low concentrations, but are inhibitory to growth at high concentrations (Microbial Ecology of Foods, V. 1, Silliker et al., (ed.) 1980. Academic Press, New York, N.Y.).

Inhibitors

Nutrient inhibitors, may include commercially available materials, especially those commonly used in the crude oil industry such as glutaraldehyde, tertiary amines, quaternary amines, Bis(tetrakis (hydroxymethyl))phosphonium sulfate, or sodium dimethyldithio-carbamate. Additional chemical inhibitors which may be suitable are described in Paulus, Wilfried. *Directory of Microbicides for the Protection of Materials—A Handbook.* Springer-Verlag, (2005). Any number of different nutrients and/or inhibitors may be used for this purpose. In one preferred embodiment, such nutrients and/or inhibitors consist of sodium lactate at 1300 ppm plus sodium nitrate at 2600 ppm plus benzalkonium chloride at 1% w/v. Ideally, the inhibitor(s) would prevent microbes from growing on the nutrients in transit, allowing further penetration into the formation before microbial growth is stimulated.

In another embodiment, where the nutrients required for an inhibited formulation cannot be economically or conveniently supplied at high inhibitory concentrations additional component(s) such has chemical inhibitors which may or may not have nutrient value, may be added to the nutrient composition with the primary role of inhibiting microbial growth. These chemical inhibitors may also be added to the injection water stream in chronological sequence with the nutrient composition. There are many examples of chemical microbial growth inhibitors that are used in industry, including the food, cosmetic, and water treatment industries [e.g., Disinfection, Sterilization, & Preservation, 5th Edition. S. S. Block (Ed.). 2001. Lippincott, Williams & Wilkins. Philadelphia, Pa.; Paulus, Wilfried. Directory of Microbicides for the Protection of Materials—A Handbook. Springer-Verlag: R. K. Robinson, C. A. Batt and P. D. Patel, (ed.), Encyclopedia of Food Microbiology. 1999. Academic Press, London).

Whether the INC contains chemical inhibitors or contains conventional nutrients at high, inhibitory concentrations the effect of using the INC formulated in this fashion is to protect the conserve the nutrients in the composition from being consumed during transfer to the target site location away from the injection site where activation and enhancement of the microbial population will occur.

Injection Process

The desired nutrients and/or inhibitors formulation may be injected at an injection site of a subsurface oil formation. While the implementation of the present invention may involve adding the inhibited nutrient/inhibitor package by a waterflood program, its method of addition to the well is not limited to the use of the waterflooding program. Alternative processes for addition of such formulations to the injection include, but not limited to, the use of a fluid such as an aqueous solution or gas (such as $CO_2$) or a solvent or a polymer that is injected into the subsurface oil formation by any procedure found most convenient for the specific location. Thus the invention is not limited to any particular process of introducing inhibited nutrient composition into the subsurface oil formation. To simplify the following discussion, herein, any injection carriers (i.e., any of those identified above) used for delivering the inhibited nutrient composition will be referred to as "water".

Since underground oil formations are frequently flooded with water to supply additional pressure to assist oil recovery, the inhibited nutrient composition may be added to this water to form an injection site formulation and injected into the subsurface oil formation through one or more injection wells and pressured to flow toward one or more production wells.

The amount of water introduced into the formation and the amount of microbial nutrients and/or inhibitors contained in the water will depend upon the desired results. Those skilled in the art may determine the amount needed to provide the desired results based on the teachings of this disclosure. Multiple nutrients and/or inhibitors formulations may be injected into the subterranean oil formation together or in separate injection steps. For example, a bank of water carrying one nutrients and/or inhibitors formulation may be followed by a second bank of water carrying a second batch of nutrients and/or inhibitors formulation. Another example may include injecting one water bank followed by a gas injection step, sometimes referred to as a WAG process.

In general the compositions of the invention may be delivered into the injection well by any one of the many well known methods in the art (*Nontechnical guide to petroleum geology, exploration, drilling, and production,* $2^{nd}$ edition. N. J. Hyne, PennWell Corp. Tulsa, Okla., USA, Freethey, G. W., Naftz, D. L., Rowland, R. C., & Davis, J. A. (2002); and *Deep aquifer remediation tools*: Theory, design, and performance modeling, In: D. L. Naftz, S. J. Morrison, J. A. Davis, & C. C. Fuller (Eds.); and *Handbook of groundwater remediation using permeable reactive barriers* (pp. 133-161), Amsterdam: Academic Press.)).

Design of the Injection Site Formulation and Application to the Site

Prior to the injection of the INC alone or as an element of an injection site formulation, certain site treatment parameters will be reviewed and analyzed. It will be useful to understand for example the dispersion rate of subsurface water from the injection site the composition oil at the oil well site to opposite absorption rates of chemical inhibitors that may be in the INC; and the composition of subterranean fluids (water, oil and water/oil mix) as they would impact the hydrolysis rates of the chemical inhibitors in the INC. Once these parameters are determined they will inform the person of skill in the art as to how best to prepare and formulate the INC and injection site formulation for the most effective use at the site.

The INC and injection site formulation will be designed such that a) consumption of nutrients will be prevented in transit to the target site, but b) there will be relief from the inhibitory effects of the composition on the local microbial population once the composition reaches the target site. For example, organic compounds that are potential growth substrates for microbial growth at lower concentration, but are inhibitory at higher concentrations, are inhibitory to microbial growth for at least 5 days. During this inhibition period, nutrients are protected from consumption by the local microorganisms, while injection liquid flow carries the nutrients to the targeted contaminated location. This formulation, results in greater activation of the decontaminating microbes upon release from inhibition by providing nutrients when they are needed. A variety of nutrients such as lactate, urea, glycerol, formate, inorganic salts, etc. may be used for halting microbial growth at the injection site and allow sufficient time for the inhibited nutrient composition to be transported to the desired remediation location. Similarly industrial preservatives (e.g., phenol, benzalkonium chloride, methylparaben, etc.) may be used to inhibit growth of the microorganisms until the preservative is eventually dissipated thus allowing time for the inhibited nutrient composition to reach the desired remediation location.

Figure 1:
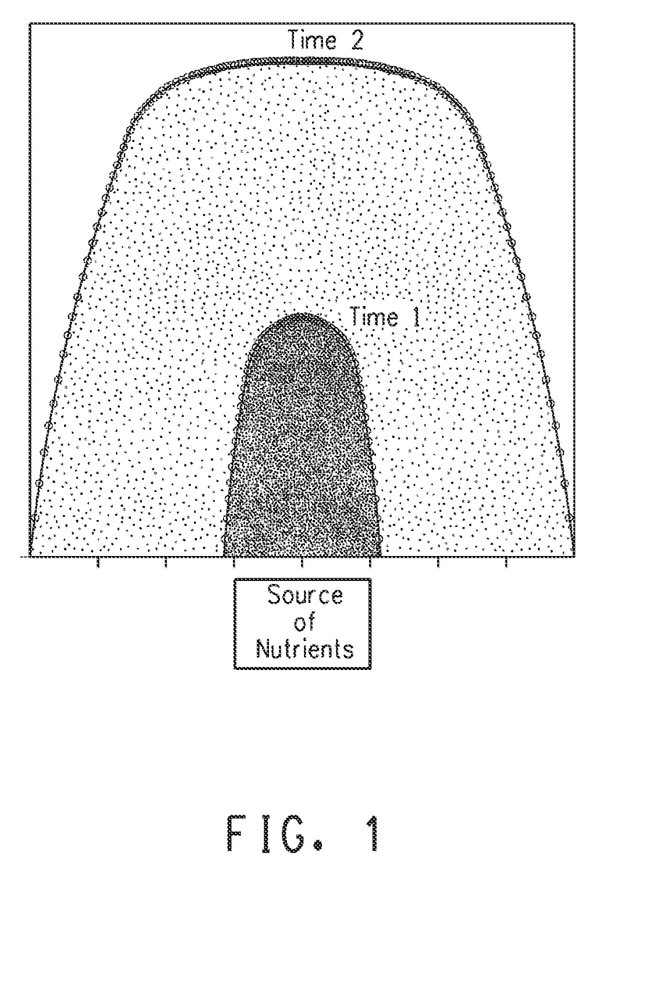
FIG. 1 is a two-dimensional representation of radial transport in an oil well formation. With time the transported material has expanded its radius of distribution approximately three-fold from the site of application of the nutrients. The concentration has declined by 6.7-fold as shown by the change in area under the data points. Total area under the gray (Time 2) region equals 4868 area units. Total area under the black region (Time 1) equals 723 area units.

Relief of inhibition may occur via a number of different mechanisms. For example, the process may be designed to allow natural dispersion in the underground formation to dilute the inhibitory compound, allowing growth on the nutrients. Field measurements of dispersion rates by methods known in the art allow one to calculate the depth at which sufficient dilution will occur to allow activation. D. Schulze-Makuch, *Ground Water,* 43:443-456, 2005). Typically, radial transport (advection with the groundwater flow, hydrodynamic dispersion, and molecular diffusion) of the inhibiting substances will eventually cause the inhibitor(s) to reach a low concentration, where inhibition is relieved (i.e., dilution relieves the inhibition). Taking advantage of radial transport also allows the MEOR and/or remediation process to occur over a larger area. For example, as illustrated in FIG. 1, relief of inhibition and subsequent growth at the nutrient front at Time 2 yields a perimeter of MEOR activation approximately 2.5-fold as long as that seen in the faster growth scenario (no or little inhibition) illustrated as Time 1.

Alternatively, the process may be designed to allow chemical alterations of the inhibitory compound to relieve inhibition. For example, chemicals such as esters will hydrolyze in water. The rates of hydrolysis are dependent on temperature and pH. Additionally, partitioning of inhibitor into the oil phase, which may occur for some inhibitors may also relieve inhibition by lowering the inhibitor concentration in water. Information from standard texts (e.g., W J Lyman, W F Reehl, D H Rosenblatt, 1990 Handbook of Chemical Property Estimation Methods, ACS, Washington, D.C.) or empirical data allow one to estimate the hydrolysis rates. The rate estimates are used to design the process such that relief from inhibition due to inhibitor hydrolysis occurs at the desired depth in the formation. Also, chemical concentration may be altered by adsorption into the oil phase of an oil formation, resulting in decreased concentrations in the water phase. Information from standard texts (e.g., J. Sangster, 1997, Octanol-Water Partition Coefficients: Fundamentals and Physical Chemistry. John Wiley and Sons) or empirical data allow one to estimate partition coefficients, or to estimate the rate at which the inhibitor will be adsorbed from the water phase. The targeted microbial activation process can then be designed around inhibitor dissipation rates and subterranean water flow rates to allow an inhibited nutrient composition to activate microbial growth at the desired depth of the subsurface oil formation or, in the case of bioremediation, the contaminated subsurface formation. It will be appreciated by the skilled person that the present method has application not only for improving oil recovery at oil well sites but also in the area of remediating contaminated sites that are infused with pollutants and contaminating compounds. So for example the inhibited nutrient compositions of the invention may be applied to ground water and subsurface geological regions contaminated with biodegradable chemicals such as various hydrocarbons or crude oil. Typically, injection wells are used to gain access to contaminated subsurface locations (e.g., G. D. Hopkins, J. Munakata, L. Semprinl, P. L. McCarty., Environ. Sci. Technol., 27: 2542-2547, 1993). Often direct drilling of the injection well into the contaminated subsurface location is prevented by local geography or property ownership issues. In these situations an injection well is drilled distant from the direct injection location and, upon establishment of proper pressure gradients by methods known to those in the art, injection liquid flow allows nutrients needed to activate decontaminating microbes to migrate from the injection site to the location of subsurface contamination. When the inhibited nutrient composition is added to the material injected at the injection well, the presence of inhibitors in the inhibited nutrient composition prevents uptake of nutrients in the composition by the natural microflora at the injection site, allowing time for the inhibited nutrient composition to be transported, without loss, to the location where remediation is required.

Depending on the nature of the site to be treated and the make up of the indigenous microbial populations it may be useful to include live microbial cultures in the injection well formulation. These cultures would be selected to act on the elements of the target site, whether that be for the purpose of remediating the site of contaminating compounds or the enhancement of oil recovery from the site. Methods of selecting appropriate microorganisms for injection into a site are common and well known in the art. See for example U.S. Pat. No. 7,472,747 and commonly owned U.S. Ser. No. 12/194,794.

Whether the use is oil recovery or remediation the application of INC's and injection site compositions may be monitored by periodically taking samples of the contaminated environment, extracting the contaminants, and analyzing the extract using methods known to one skilled in the art.

Benefits of the Use of INC

Use of an INC at an oil well site has significant benefits over the current processes used which often result in enhancement of the local microbial population at the injection site, resulting in plugging the formation surface or increasing the levels of toxic microbial by products.

For example, control of the linear velocity of the injected water in the well piping-oil formation system, which is dependent on the pump capacity, has been the primary reported approach for targeting microbial activation (for example see RU2060371). This approach poorly controls time, location, and character of microbial activation. When nutrient components are just injected into the well, flow control does not protect nutrients consumption by native strains in transit. Activation of native strains in uncontrolled locations may result in undesirable outcomes. For example, the velocity drop at the subsurface oil formation face allows preferential microbial growth at the face, potentially plugging the formation face, causing increased back pressure and decreased water flow (T L Stewart & D-S Kimb, Modeling of biomass-plug development and propagation in porous media, Biochem. Eng., 17:107-119, 2004). Subsurface oil formation face plugging potentially reduces oil production.

In wells with high sulfate concentrations in the injection water, growth of native, sulfate-reducing bacteria may increase levels of the toxic by-product, hydrogen sulfide, in the well. Growth of native strains may also increase corrosion rates in the well piping. Also, in cases where an introduced microbial formulation must be activated to achieve the desirable chemical changes in the oil reservoir, depletion of the nutrient package by native microbes reduces the potential growth of the introduced microbes, thus lowering the oil mobilization efficiency. Alternatively, uncontrolled consumption of the nutrients by the introduced microbial populations may lead to activation of the microorganisms before entry into the oil formation, thus decreasing the effectiveness of the process in oil mobilization.

The methods of the present invention overcome the above noted difficulties and provide an advance in the art of microbial enhanced oil recovery and remediation of contaminated sites.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

The following abbreviations have the meaning as set forth as follows: ""ml" means milliliter, "g/L' means gram per liter, "° C." means degrees Celsius, "mg/L" means milligram per liter, "%" means percent' "ppm/day" means parts per million per day, "h" means hour(s), "mD" means milliDarcy, "m" means meter, "$m^2/S$" means square meter per second.

Growth of Microorganisms for Use in Laboratory Scaled Examples

Aerobic Growth—

Typically cells were grown at a temperature in the range of about 25° C. to about 40° C. in an appropriate medium. Suitable growth medium in the present invention contained: $Na_2HPO_4.7H_2O$, 1.4 g/L, $KH_2PO_4$, 0.69 g/L, $NH_4Cl$, 0.5 g/L, $MgSO_4.7H_2O$, 0.1/L g, SL-10 trace metals [per liter, HCl (25%; 7.7 M), 10.00 ml, $FeCl_2.4 H_2O$, 1.50 g, $ZnCl_2$, 70.00 mg, $MnCl_2.4H_2O$, 100.00 mg, $H_3BO_3$, 6.00 mg, $CoCl_2.6 H_2O$, 190.00 mg, $CuCl_2.2H_2O$, 2.00 mg, $NiCl_2.6 H_2O$, 24.00 mg, $Na_2MoO_4.2 H_2O$, 36.00 mg], 10 ml, NaCl, 7.5 g/L, $NaHCO_3$, 1 g/L, sodium lactate, 10 g/L, yeast extract, 5 mg/L, which supported aerobic growth at 30° C.

Anaerobic Growth—

Techniques for growth and maintenance of anaerobic cultures are described in "Isolation of Biotechnological Organisms from Nature", (Labeda, D. P. ed. 117-140, McGraw-Hill Publishers, 1990). For denitrification, anaerobic growth is measured by nitrate depletion from the growth medium over time. Nitrate is utilized as the primary electron acceptor under the growth conditions used herein. The reduction of nitrate to nitrogen has been previously described (Moreno-Vivian, C., et al., J. Bacteriol., 181: 6573-6584, 1999). In some cases nitrate reduction processes lead to nitrite accumulation which is subsequently further reduced to nitrogen. Accumulation of nitrite is therefore also considered evidence for active growth and metabolism by microorganisms. Depletion of nitrite is also evidence of growth and metabolism by microorganisms.

In this invention, the anaerobic growth and survival was tested in 20 ml crimp-capped anaerobic vials, using a complete nutrient medium of the following composition: $Na_2HPO_4.7H_2O$, 1.4 g/L, $KH_2PO_4$, 0.69 g/L, $NH_4Cl$, 0.5 g/L, $MgSO_4.7H_2O$, 0.1/L g, SL-10 trace metals, 10 ml, NaCl, 7.5 g/L, $NaHCO_3$, 7.2 g/L, sodium nitrate, 12 g/L, Na lactate, 7 g/L, yeast extract, 10 mg/L, pH 7.3-7.8.

Example 1

Controlled MEOR Activation—High Concentrations of Growth-Supporting Nutrients are Inhibitory to Oil Well-Associated Microbes The purpose of this Example was to demonstrate that high concentrations of nutrients could inhibit microbial growth. *Pseudomonas stutzeri* strain LH4:15, ATCC PTA-8823 which is found in oil wells on the North Slope of Alaska, was used as the test strain in this Example. The nutrient medium described above supported aerobic growth at 30° C. Additional potential microbial nutrients were added at various concentrations as outlined in Table 1. Growth was monitored visually with positive growth indicated by moderate to heavy turbidity. As shown in Table 1, although sodium nitrate and urea, commonly used nitrogen sources for microbial growth, were permissive for growth at low concentrations, at ≥100 g/L for sodium nitrate and ≥50 for urea, microbial growth was inhibited. Similarly, a variety of organic compounds that are potential growth substrates at lower concentrations proved inhibitory for at least five days at higher tested concentrations. Results obtained in these experiments underline the potential of applying high concentrations of nutrients to prevent consumption of the applied nutrients by microbial populations prior to its reaching the desired microbial population at the targeted depth in the subsurface oil formation or contaminated subsurface. Therefore in situations where either storage is needed or delays are required to allow nutrient activation of the target microbial population, high concentrations of nutrients to stabilize stored nutrients until needed and protect nutrients in transit would be applicable.

TABLE 1

Growth response over time to varying concentrations of potential microbial nutrients.

| | | Hours of incubation | | |
|---|---|---|---|---|
| Nutrient | g/L | 24 | 48 | 120 |
| NaNO₃ | 10 | ++ | ++ | ++ |
| | 20 | ++ | ++ | ++ |
| | 50 | − | + | ++ |
| | 100 | − | − | − |
| | 200 | − | − | − |
| Na lactate | 10 | ++ | ++ | ++ |
| | 20 | ++ | ++ | ++ |
| | 50 | − | − | − |
| | 100 | − | − | − |
| | 200 | − | − | − |
| Urea | 10 | ++ | ++ | ++ |
| | 20 | ++ | ++ | ++ |
| | 50 | − | − | − |
| | 100 | − | − | − |
| | 200 | − | − | − |
| Glycerol | 10 | ++ | ++ | ++ |
| | 20 | ++ | ++ | ++ |
| | 50 | ++ | ++ | ++ |
| | 100 | ++ | ++ | ++ |
| | 200 | − | − | − |
| Ethylene glycol | 10 | ++ | ++ | ++ |
| | 20 | ++ | ++ | ++ |
| | 50 | ++ | ++ | ++ |
| | 100 | + | ++ | ++ |
| | 200 | − | − | − |
| Ethyl formate | 0.1 | ++ | ++ | ++ |
| | 0.5 | ++ | ++ | ++ |
| | 1 | ++ | ++ | ++ |
| | 5 | + | ++ | ++ |
| | 25 | − | − | − |
| | 50 | − | − | − |
| Octanol | 0.001 | ++ | ++ | ++ |
| | 0.005 | ++ | ++ | ++ |
| | 0.01 | ++ | ++ | ++ |
| | 0.05 | ++ | ++ | ++ |
| | 0.25 | − | − | − |
| | 0.5 | − | − | − |
| Ethanol | 0.05 | ++ | ++ | ++ |

TABLE 1-continued

Growth response over time to varying
concentrations of potential microbial nutrients.

| Nutrient | g/L | Hours of incubation | | |
|---|---|---|---|---|
| | | 24 | 48 | 120 |
| | 0.1 | ++ | ++ | ++ |
| | 0.5 | ++ | ++ | ++ |
| | 1 | ++ | ++ | ++ |
| | 10 | ++ | ++ | ++ |
| | 20 | + | ++ | ++ |
| | 50 | − | − | − |

− = no turbidity
+ = slight turbidity
++ = moderate to heavy turbidity.

Example 2

Industrial Preservatives Inhibit Oil Well-Associated Microbes

The purpose of this Example was to demonstrate that industrial preservatives could inhibit growth of microorganisms associated with oil wells. *Pseudomonas stutzeri* strain LH4:15 (ATCC PTA-8823) was grown as outlined in Example 1. Various preservatives commonly used in the food, cosmetic, and water treatment industries were tested for their inhibitory effect at various concentrations (Table 2). Growth was monitored visually and positive growth was indicated by moderate to heavy turbidity. As shown in Table 2, with the exception of phenol, the commercial preservatives were effective at preventing growth of the test strain when present at 1 g/L or greater. Thus, these chemicals offer another option for controlling microbial growth. Their advantage over the nutrients used in Example 1 is that they could be used at a much lower concentration compared to those required for the nutrients in Example 1.

TABLE 2

Growth response to varying concentrations of industrial preservatives

| Compound | g/L | growth |
|---|---|---|
| phenol | 0.01 | ++ |
| | 0.05 | ++ |
| | 0.1 | ++ |
| | 0.5 | ++ |
| | 1 | ++ |
| | 10 | − |
| | 50 | − |
| Benzalkonium chloride | 0.0001 | ++ |
| | 0.001 | ++ |
| | 0.005 | ++ |
| | 0.01 | ++ |
| | 0.1 | − |
| | 0.5 | − |
| | 1 | − |
| N,N,-dimethyldodecylamine | 0.0001 | ++ |
| | 0.001 | ++ |
| | 0.005 | ++ |
| | 0.01 | ++ |
| | 0.1 | − |
| | 0.5 | − |
| | 1 | − |
| Methylparaben | 0.01 | ++ |
| | 0.05 | ++ |
| | 0.1 | ++ |
| | 0.5 | + |
| | 1 | − |
| | 2.5 | − |

TABLE 2-continued

Growth response to varying concentrations of industrial preservatives

| Compound | g/L | growth |
|---|---|---|
| 4-chloro-3-metyhl phenol | 0 | ++ |
| | 0.1 | − |
| | 0.5 | − |
| | 1 | − |
| sodium dithiodimethyl carbamate | 0 | ++ |
| | 0.1 | ++ |
| | 0.2 | ++ |
| | 0.3 | − |
| | 0.5 | − |
| | 0.8 | − |
| | 1 | − |
| 2-phenoxy-ethan-1-ol | 0 | ++ |
| | 1 | ++ |
| | 2 | ++ |
| | 3 | ++ |
| | 4 | − |
| Bis(tetrakis(hydroxymethyl))phosphonium sulfate | 0 | ++ |
| | 0.1 | ++ |
| | 0.2 | ++ |
| | 0.3 | − |
| | 0.4 | − |

− = no turbidity
+ = slight turbidity
++ = moderate to heavy turbidity

Example 3

Determination of Biocidal Versus Biostatic Inhibition

Examples described above demonstrate that high concentrations of nutrient salts or organic nutrients and industrial preservatives, will inhibit growth of oil well-associated microbes on nutrient mixtures that typically support growth. The nature of this inhibition, whether bacteriocidal (killing) or bacteriostatic (slowing microbial growth), is important to optimizing the activation of MEOR processes within the oil formation or bioremediation within the contaminated subsurface formation. The purpose of this Example was to demonstrate whether growth inhibition was due to bacteriocidal or bacteriosatic effects of the inhibitory compounds used. A number of inhibitory formulations, which mimic formation conditions under anaerobic conditions, were therefore tested.

The anaerobic growth and survival was tested as outlined above. The inhibitors were added to the 20 ml crimp-capped anaerobic vials at various concentrations (Table 3) and included a set of control vials that did not contain any compounds at inhibitory concentrations. Vials were inoculated using an overnight aerobic culture of *Pseudomonas stutzeri* strain LH4:15 (ATCC PTA-8823) in Luria Bertani medium (LB, Mediatech Inc., Herndon, Va.,) at a final $OD_{600}$ of 0.05. Within 2 hours of inoculation, serial dilutions from each treatment vial were made into aerobic LB medium to determine the cell numbers at Day 0. After approximately 24 hours cell numbers were estimated by noting the highest positive dilution based on the presence or absence of turbidity in dilutions of $10^{-1}$ to $10^{-11}$ in the serial dilution plates. Cell numbers on Day 0 and Day 7 were measured to obtain a survival estimate during inhibitor exposure.

Some inhibitors at higher concentrations rapidly killed the test microorganism. For example benzalkonium chloride at 0.1 g/L or greater killed the cells on Day 0 (Table 3). In general, higher inhibitor concentrations caused greater losses in cell number between Day 0 and Day 7 (Table 3).

Some inhibitors such as octanol were ineffective except at the highest concentrations as indicated by the significant increase in $OD_{600}$ from the starting value of 0.05 (Table 3). A number of inhibitors and concentrations showed the desired inhibition with minor cell killing. Methylparaben showed this desirable property at the lowest efficacious concentrations (Table 3). Comparison of final and starting $OD_{600}$ gives a measure of growth. Vials reaching or exceeding control $OD_{600}$ experienced no inhibition. In situations where a microbial inoculum accompanies the inhibited nutrient composition package, bacteriostatic inhibitors allow protection from nutrient consumption in transit without killing the inoculant.

TABLE 3

Effect of various inhibitors on the growth of
*Pseudomonas stutzeri* strain LH4:15(ATCC PTA-8823)
Starting vial optical density, $OD_{600}$ = 0.05

| Compound | g/L | change in Log cell number | Final anaerobic vial OD |
|---|---|---|---|
| NaCl | 50 | −1 | 0.08 |
|  | 80 | −3 | 0.11 |
|  | 100 | −1 | 0.05 |
|  | 200 | −2 | 0.03 |
|  | 400 | −4 | 0.03 |
| NaNO₃ | 50 | −1 | 0.06 |
|  | 80 | 0 | 0.03 |
|  | 100 | −2 | 0.02 |
|  | 200 | −6 | 0.03 |
|  | 400 | −5 | 0.03 |
| Urea | 20 | −1 | 0.2 |
|  | 30 | −1 | 0.13 |
|  | 50 | −1 | 0.03 |
|  | 100 | −1 | 0.02 |
|  | 200 | Dead | 0.01 |
|  | 300 | Dead | 0.01 |
| Ethylformate | 5 | −2 | 0.02 |
|  | 10 | −6 | 0.01 |
|  | 25 | −6 | 0.005 |
|  | 50 | Dead | 0.05 |
|  | 80 | Dead | 0.06 |
| benzalkonium Cl | 0.01 | 0 | 0.12 |
|  | 0.04 | 0 | 0.01 |
|  | 0.08 | −4 | 0.02 |
|  | 0.1 | Dead | 0.02 |
|  | 0.5 | Dead | 0.06 |
|  | 1 | Dead | 0.32 |
| Octanol | 0.05 | 0 | 0.28 |
|  | 0.1 | −1 | 0.4 |
|  | 0.2 | 0 | 0.54 |
|  | 0.25 | −1 | 0.4 |
|  | 0.5 | −1 | 0.01 |
| Methyl paraben | 0.5 | 0 | 0.09 |
|  | 0.6 | 0 | 0.05 |
|  | 0.8 | 1 | 0.05 |
|  | 1 | −1 | 0.04 |
|  | 2.5 | −2 | 0.01 |
| Control | 0 | −1 | 0.23 |
| Control | 0 | −1 | 0.21 |
| Control | 0 | −1 | 0.18 |

Log change = log day 0 cell number minus log day 7 cell number.
"Dead" indicates instantaneous killing of the cells upon inhibitor addition on day 0.

Example 4

Inhibition Relief VIa Inhibitor Instability

The following Example demonstrates how ethyl formate delays nutrient consumption until eventual hydrolysis leads to relief of inhibition and consumption of microbial nutrients. The growth delay allows deeper penetration into the oil well formation and more widespread MEOR activation. Injection water for the North Slope of Alaska was used to demonstrate the relief of growth inhibition via hydrolysis of ethyl formate.

Injection water was amended with sodium nitrate as electron acceptor plus a growth substrates. In addition 0.2% ethyl formate was added to the inhibited treatment. The injection water was incubated anaerobically at approximately 25° C. under an atmosphere of 80% nitrogen and 20% carbon dioxide, reflecting typical growth conditions in the North Slope oil well formations. Growth of the native populations, nitrate concentrations and ethyl formate concentrations were monitored over two weeks.

Figure 2:
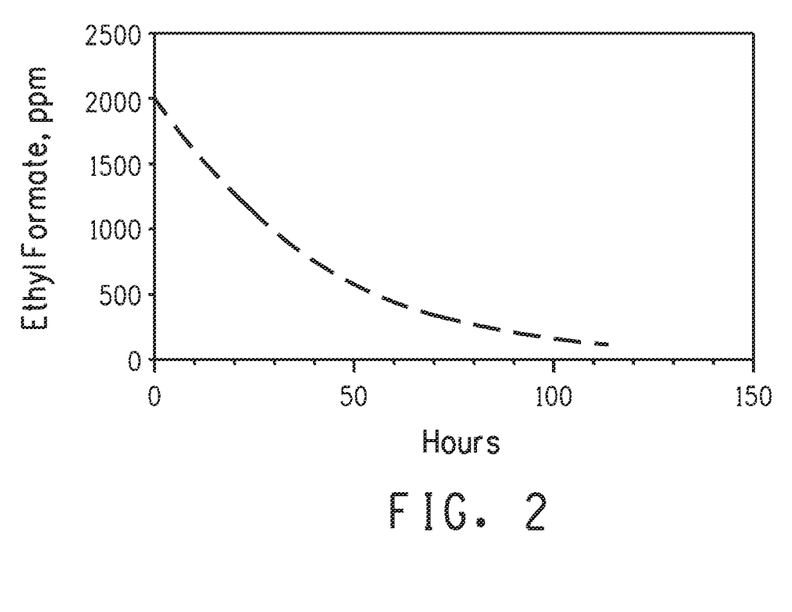
FIG. 2 is a graph illustrating the decline of the ethyl formate added to the injection water for the North Slope of Alaska containing sodium nitrate and a growth substrate. Ethyl formate concentrations declined 10-fold in about four days. (Example 4).
Figure 3:
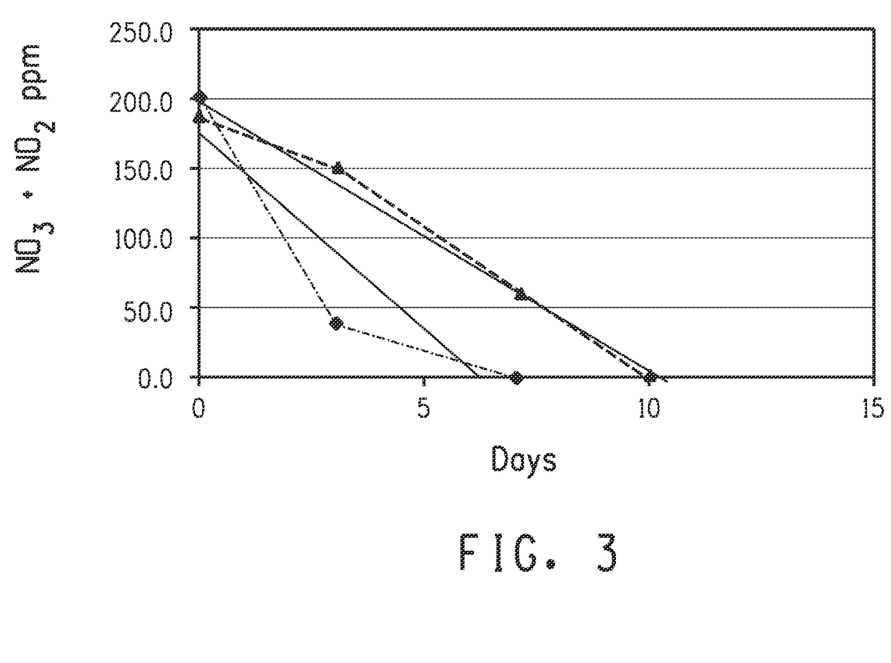
FIG. 3 is a graph illustrating the loss of $NO_3+NO_2$ over time. Black diamonds are the measured values for the treatment without added ethyl formate. White triangles are the measured values for the treatment with 0.2% ethyl formate added. Actual concentrations in the treatment vials are 10× indicated, because analyzed samples were diluted 10-fold. Straight lines indicate the mean rate of loss in each treatment. (Example 4)
Figure 4:
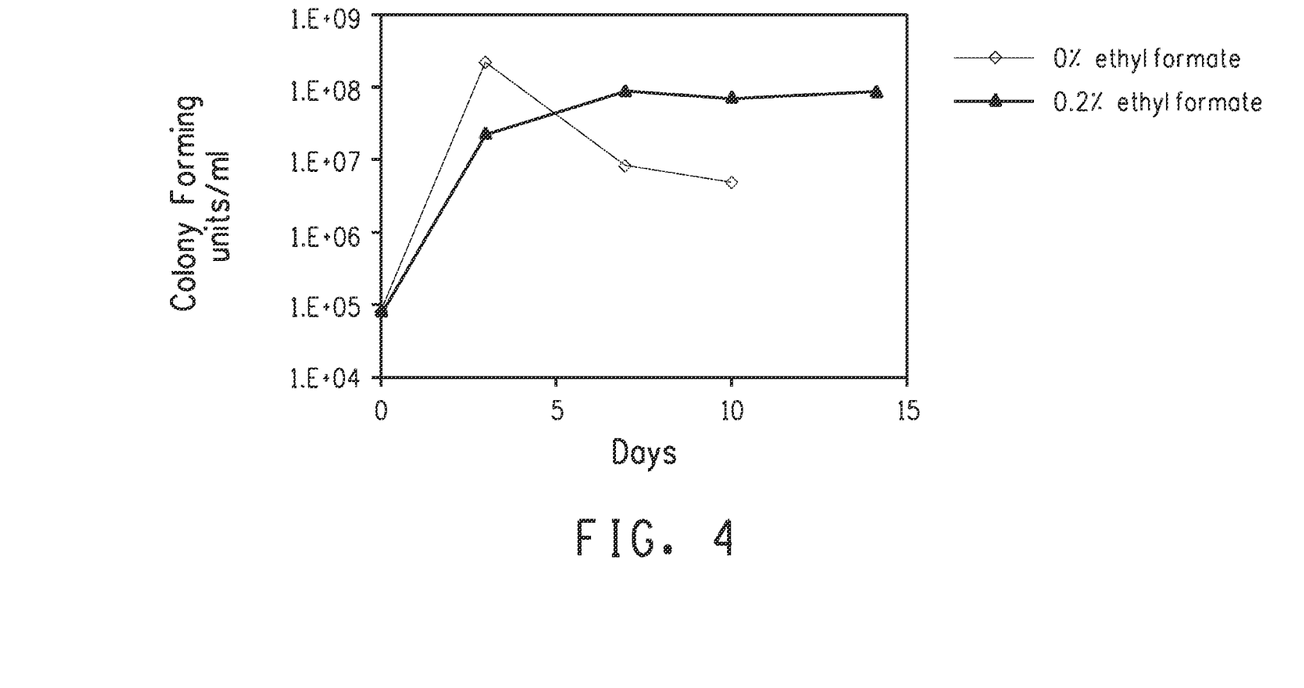
FIG. 4 is a graph illustrating the number of colony forming units of the native anaerobic population in the injection water from the North Slope of Alaska, growing anaerobically with added nitrate and lactate as nutrients, in the absence and presence of ethyl formate. Delayed increases in colony forming units in the treatment with 0.2% ethyl formate demonstrate microbial growth inhibition by ethyl formate. White diamonds show 0% ethyl formate and black triangles show 0.2% ethyl formate (Example 4).

Ethyl formate concentrations declined 10-fold in about four days (FIG. 2). During this period ethyl formate significantly slowed down microbial growth. Consumption of electron acceptors, nitrate ($NO_3^-$)+nitrite ($NO_2^-$), was 31% slower in the inhibited treatment (FIG. 3). Mean nitrate ($NO_3^-$)+nitrite ($NO_2^-$) loss rates were 274 ppm/day for no added ethyl formate, 190 ppm/day for 0.2% ethyl formate. Ethyl formate at 0.2% concentration, delayed maximum growth by four days and resulted in longer maintenance of the maximum population (FIG. 4). In the field, the injection water flow moves the nutrients deeper into the formation during this delay, hence allowing nutrients to penetrate into a deeper and more widespread location in the oil formation for the MEOR process.

Example 5 (Prophetic)

Figure 5:
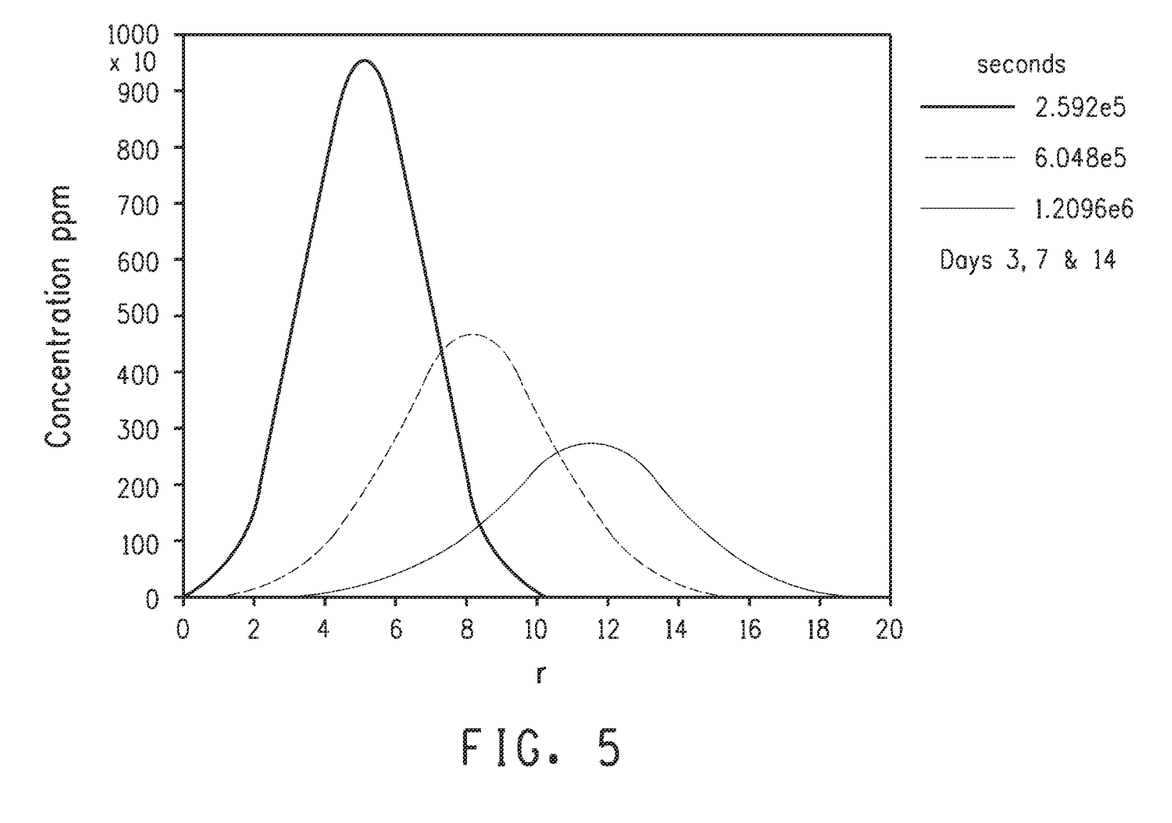
FIG. 5 is a graph illustrating the estimated concentrations in ppm of either of urea or sodium lactate injected at into the oil well at 50,000 ppm for 20 hours on day 0. Injected nutrients are 50,000 ppm urea+50,000 ppm sodium lactate, Model parameters, representing the geology of the subsurface formation, are porosity=30%, permeability=200 mD, longitudinal dispersivity=0.83 m, transverse dispersivity=0.083 m, molecular diffusivity=$10^{-8}$ $m^2/s$. r=radius of travel from injection point, meters. The y-axis indicates concentration, ppm, shown at three different times (2.592× 105 seconds, 6.048×105 seconds, and 1.2096×106 seconds), after the 20 h injection pulse, as shown by the three different curves (Example 5).

High Concentrations of Growth-Supporting Nutrients Prevent Microbial Growth and Blinding of the Oil Formation Face to Target MEOR Processes Deeper in the Oil Formation The purpose of this prophetic Example is to show that high concentrations of growth-supporting nutrients may prevent growth, thus allowing penetration of the desired microorganisms deeper into the formation for an improved MEOR process. For example, urea (nitrogen source), and sodium lactate (growth substrate), each at 50 g/L concentration, may be added in combination to the injection water stream. This combination may be pumped into the formation for 20 hours. The additive effects of these nutrients initially cause inhibition of the growth of microbial populations in the oil well formation. As illustrated in Example 1 until the combined concentration of these nutrients reduces to 10-20 g/L, microbial growth is inhibited. Using physical parameters common in oil well formations found in unconsolidated sandstone regions of the North Slope, hydrogeological modeling determines that it will take approximately three days or more for transport (advection with the groundwater flow, hydrodynamic dispersion, and molecular diffusion) to dilute any component used initially at 50 g/L down to 10 g/L (FIG. 5). Microbial growth targeted away from the formation face by the inhibitory effect of high nutrient concentrations occurs when high concentrations are diluted, for example when the combined concentrations of added nutrients reaches 20 g/L or less (10 g/L or less for each compound). After about a week a slight backpressure rise is observed at the wellhead indicating that microbial growth has started and formation pores are starting to block. This results in a MEOR region on the order of nine fold larger (radius, r, is approximately equal to three and the surface area of a sphere is a function of the square of the radius) than growth at the oil formation face (FIG. 5). This targeted microbial growth plugs larger pores in the formation and diverts injection water flow into previously untouched regions resulting in increased oil production via entrainment of previously unavailable oil.

Example 6 (Prophetic)

Figure 6:
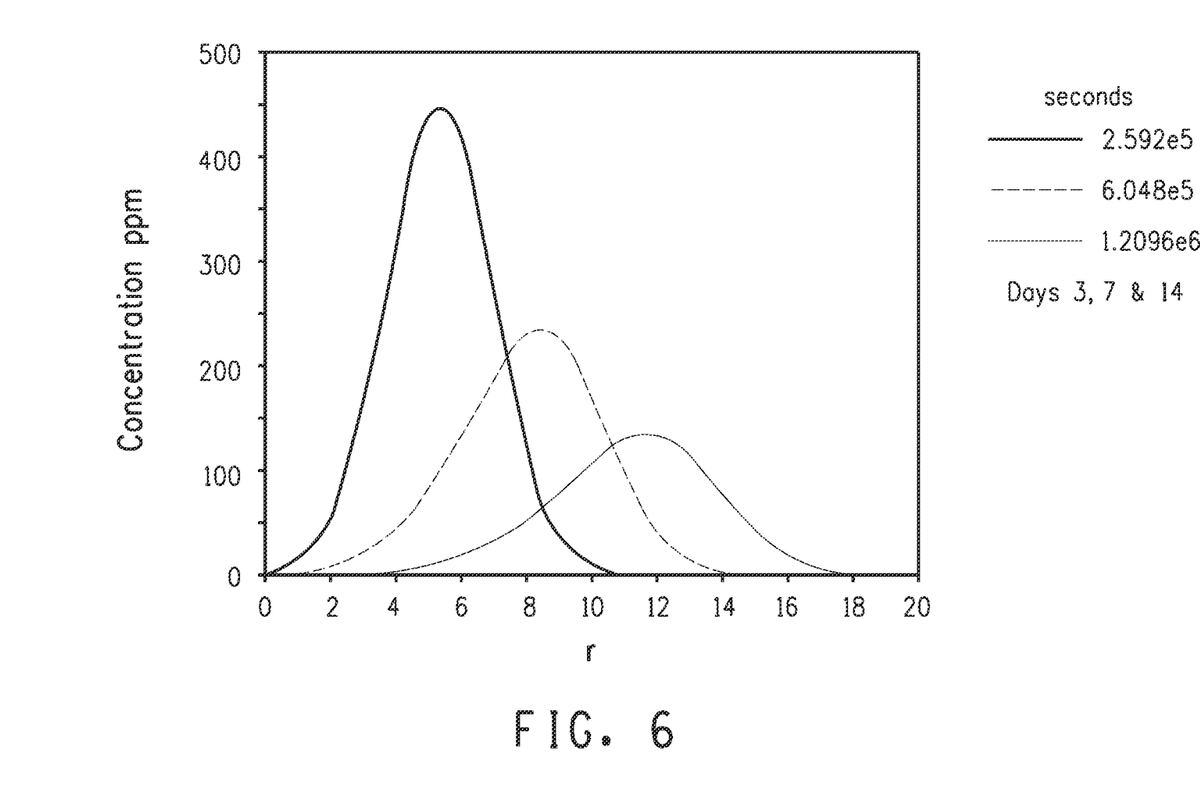
FIG. 6 is a graph illustrating the estimated concentrations in ppm of sodium dimethyldithio-carbamate injected into the oil well at 10,000 ppm for 5 hours on day 0. Model parameters, representing the geology of the subsurface formation, are porosity=30%, permeability=200 mD, longitudinal dispersivity=0.83 m, transverse dispersivity=0.083 m, molecular diffusivity=$10^{-8}$ $m^2/s$. r=radius of travel from injection point, meters. The y-axis indicates concentration, ppm, shown at three different times (2.592×105 seconds, 6.048×105 seconds, and 1.2096×106 seconds), after the 20 h injection pulse, as shown by the three different curves (Example 6).

Industrial Preservatives Inhibit Growth and Prevent Blinding of the Formation Face and Target MEOR Processes Deeper in the Oil Formation The purpose of this prophetic Example is to show that industrial preservatives, at various concentrations, may prevent growth, thus allowing penetration of the nutrient package to the desired subterranean microbial population deeper into the oil formation. This allows for an improved MEOR process. For example, nitrate as a nitrogen source and electron acceptor and glucose as a growth substrate, each at 25 g/L concentration, may be added in combination to the injection water stream. In addition, sodium dimethyldithiocarbamate, at 1% concentration, may be added to this nutrient mixture. This combination may be pumped into the formation for 5 hours. The industrial biocide causes inhibition of the growth of microbial populations in the oil well formation independent of the added nutrient concentrations. As illustrated in Example 2 until the sodium dimethyldithiocarbamate reaches a concentration of <0.1 g/L, microbial growth is inhibited. Using physical parameters common in oil well formations found in unconsolidated sandstone regions of the North Slope, hydrogeological modeling determines that it will take approximately fourteen days for flow dispersion to dilute sodium dimethyldithiocarbamate to approximately 0.1 g/L (FIG. 6). Microbial growth targeted away from the oil formation face by the inhibitory effect of the industrial preservative occurs when it is dispersed. No backpressure rise is observed at the wellhead because of the depth at which MEOR region develops. However, the MEOR region is greater in size than in Example 5 because greater nutrient dispersion occurs before sodium dimethyldithiocarbamate reaches a concentration permissive for microbial growth (FIG. 6). This targeted microbial growth plugs larger pores in the oil formation and diverts injection water flow into previously untouched regions resulting in increased oil production via entrainment of previously unavailable oil.

Example 7 (Prophetic)

Inhibitor Dissipation Via Phase Partitioning

The purpose of this prophetic Example is to show that industrial preservatives, at various concentrations, may prevent growth, thus allowing penetration of the desired microorganisms deeper into the formation for an improved MEOR process. In this Example a contribution to inhibitor dissipation made by adsorption of the inhibitor into the oil phase may be observed. For example, nitrate as a nitrogen source and electron acceptor and glucose as a growth substrate, each at 25 g/L concentration, may be added in combination to the injection water stream. In addition, benzalkonium chloride may be added to the inhibited nutrient composition. The composition may be pumped into the oil well formation for 5 hours. The industrial biocide inhibits growth of microbial populations in the oil well formation independent of the added nutrient concentrations. As illustrated in Example 2 until the benzalkonium chloride reaches a concentration of <0.1 g/L, microbial growth is inhibited. Using physical parameters common in oil well formations found in unconsolidated sandstone regions of the North Slope, dispersion modeling determines that it will take approximately fourteen days for flow dispersion to dilute benzalkonium chloride to approximately <0.1 g/L. In addition, it may be empirically determined, through laboratory experimentation, that the partition coefficient for benzalkonium chloride in an oil/water system is approximately 10. Therefore, rather than adding benzalkonium chloride at 2% concentration based on dispersion modeling, it is added at a 10% initial concentration to counter act losses due to adsorption. This method ensures microbial growth targeted away from the oil formation face. No backpressure rise is observed at the wellhead because of the depth at which MEOR region develops. This targeted microbial growth plugs larger pores in the oil formation and diverts injection water flow into previously untouched regions resulting in increased oil production via entrainment of previously unavailable oil.

The invention claimed is:

1. A method of enhancing the growth of microbes at targeted subsurface location comprising:
   a. providing a subsurface location comprising an injection site;
   b. providing the components of an inhibited nutrient composition selected from the group consisting of:
      i) nutrients;
      ii) chemical inhibitors; and
      iii) live microbial cultures;
   c. performing an analysis of site treatment parameters selected from the group consisting of; determining the dispersion rate of subsurface water from the injection site; analyzing the composition oil at the oil well site to determine absorption rates of the chemical inhibitors; and analyzing the composition of subterranean fluids for hydrolysis rates of the chemical inhibitors;
   d. formulating an inhibited nutrient composition comprising specific nutrient concentrations on the basis of the analysis of step c) in such that injection of the inhibited nutrient composition in fluid at the injection site results in enhanced microbial growth at a target site distant from the injection site.

2. The method of claim 1 wherein the enhanced microbial growth of step d) improves oil recovery from the targeted subsurface location.

3. The method of claim 1 wherein the enhanced microbial growth of step d) degrades contaminating compounds at the targeted subsurface contaminated location.

4. The method of claim 1 wherein the inhibited nutrient composition is injected in an injection site formulation of any of claims 1-3.

* * * * *